United States Patent
Disalvo et al.

(10) Patent No.: US 7,988,779 B2
(45) Date of Patent: Aug. 2, 2011

(54) ABSORBENT ARTICLES COMPRISING NANOPARTICLES

(75) Inventors: Anthony L. Disalvo, Bernardsville, NJ (US); Carolyn J. Mordas, Princeton, NJ (US)

(73) Assignee: McNeil-PPC, Inc., Skillman, NJ (US)

( * ) Notice: Subject to any disclaimer, the term of this patent is extended or adjusted under 35 U.S.C. 154(b) by 1260 days.

(21) Appl. No.: 10/979,364

(22) Filed: Nov. 1, 2004

(65) Prior Publication Data
US 2005/0115462 A1 Jun. 2, 2005

Related U.S. Application Data

(60) Provisional application No. 60/515,758, filed on Oct. 30, 2003.

(51) Int. Cl.
*C09C 1/62* (2006.01)
*B05D 5/00* (2006.01)
(52) U.S. Cl. .......................... 106/403; 427/199
(58) Field of Classification Search .......... 106/403; 502/400; 424/618; 427/372.2, 452, 199, 427/219, 212
See application file for complete search history.

(56) References Cited

U.S. PATENT DOCUMENTS

| | | | |
|---|---|---|---|
| 3,440,181 A | 4/1969 | Franciszek | |
| 4,449,978 A | 5/1984 | Iacoviello | |
| 4,589,876 A | 5/1986 | Van Tilburg | |
| 4,608,047 A | 8/1986 | Mattingly | |
| 4,640,810 A | 2/1987 | Laursen et al. | |
| 4,687,478 A | 8/1987 | Van Tilburg | |
| 4,739,007 A | 4/1988 | Okada et al. | |
| 4,900,320 A | 2/1990 | McCoy | |
| 5,143,954 A | 9/1992 | Hutton et al. | |
| 5,415,926 A | 5/1995 | Leighton et al. | |
| 5,576,282 A | 11/1996 | Miracle et al. | |
| 5,707,950 A | 1/1998 | Kasturi et al. | |
| 5,866,242 A | 2/1999 | Tan et al. | |
| 5,869,033 A | 2/1999 | Schulz | |
| 5,885,516 A | 3/1999 | Christensen | |
| 5,985,169 A | 11/1999 | Miller et al. | |
| 6,482,192 B2 | 11/2002 | Haarer et al. | |
| 6,492,453 B1 | 12/2002 | Ebrahimian et al. | |
| 6,497,690 B2 | 12/2002 | Haarer | |
| 6,518,324 B1 | 2/2003 | Kresta et al. | |
| 7,005,408 B2 | 2/2006 | Ahmad et al. | |
| 7,169,348 B2 | 1/2007 | Zhu et al. | |
| 7,285,517 B2 | 10/2007 | Ahmad et al. | |
| 7,758,887 B2 | 7/2010 | Ahmad et al. | |
| 2002/0055580 A1 | 5/2002 | Lorah et al. | |
| 2002/0150678 A1 | 10/2002 | Cramer et al. | |
| 2003/0114822 A1 | 6/2003 | Collando et al. | |
| 2003/0185964 A1 | 10/2003 | Weber et al. | |
| 2003/0203009 A1 * | 10/2003 | MacDonald | 424/443 |
| 2004/0175386 A1 | 9/2004 | Yoshikawa et al. | |
| 2005/0074413 A1 | 4/2005 | Belli et al. | |

FOREIGN PATENT DOCUMENTS

| | | |
|---|---|---|
| JP | 10-182142 | 7/1998 |
| WO | WO 00/78281 A | 12/2000 |
| WO | WO 02/24759 | 3/2002 |
| WO | WO 02/096380 A | 12/2002 |
| WO | WO 03/002076 | 1/2003 |
| WO | WO 2004/108589 A2 | 12/2004 |

OTHER PUBLICATIONS

International Search Report dated Mar. 2, 2005, for corresponding international application PCT/US2004/036372.

* cited by examiner

*Primary Examiner* — Anthony Green
*Assistant Examiner* — Pegah Parvini

(57) ABSTRACT

The present invention relates to soft surface coatings and absorbent articles comprising composite materials that are functionalized nanoparticles and in particular, metal-loaded nanoclays. In one embodiment, the metal is silver and the nanoparticle comprises a nanoclay. Silver ion is reduced to its neutral metal state ($Ag^0$) and loaded onto the nanoclay.

2 Claims, 1 Drawing Sheet

ABSORBENT ARTICLES COMPRISING NANOPARTICLES

CROSS-REFERENCE TO RELATED APPLICATION

This application claims priority from U.S. provisional application Ser. No. 60/515,758 filed Oct. 30, 2003.

FIELD OF THE INVENTION

The present invention relates to soft surface coatings and absorbent articles comprising composite materials that are functionalized nanoparticles and in particular, metal-loaded nanoclays.

BACKGROUND OF THE INVENTION

For centuries, silver metal has been known to be an agent capable of killing many different microbial species. It was commonly used to purify drinking solutions or administered to sick individuals before the existence of modern antibiotics. Even after the discovery of penicillin and its descendents, colloidal silver solutions were often used in cases in which troublesome bacteria had become resistant to antibiotics.

Colloidal silver solutions are commercially available today. They are often unstable, however, and have a short shelf life. This is due to the tendency of the silver particles to aggregate and form clusters so large that they are no longer suspended in solution. For this reason, undesirable gelling agents are added to solutions to keep the silver particles suspended by preventing particle aggregation. Another problem of the commercially available solutions is that the majority of the silver content is usually found to be silver ions. This poses a large problem in medical applications where silver ions rapidly combine with ubiquitous chloride to form an insoluble white precipitate.

Nanoparticles have been known to be used as fillers as disclosed in U.S. Pat. No. 6,492,453, as coatings as disclosed in U.S. Ser. No. 2003/0185964 and as foam components as disclosed in U.S. Pat. No. 6,518,324.

Nanoparticle systems are disclosed in U.S. Ser. No. 2002/0150678 as being used in a composition and a method to impart surface modifying benefits to soft and hard surfaces. In particular, this application discloses a soft surface coating for articles such as fabrics and garments.

Inorganic particulates, such as, clays, silicates, and alumina have been widely used in combination with adjunct detergent and laundry compounds to impart some form of antistatic control and/or fabric softening benefit.

The present invention relates to composite materials comprising metal loaded onto exfoliated nanoparticles. Such functionalized nanoparticles may be incorporated into soft surface coatings to enhance or modify their bulk physical and performance characteristics. Such soft surface coatings may in turn be used in the preparation of absorbent articles with improved properties. Addition of the coatings to for example the absorbent core of a disposable, absorbent article may help control malodor formation and increase absorbency.

In one embodiment, the metal is silver and the nanoparticle comprises a nanoclay. Silver ion is reduced to its neutral metal state ($Ag^0$) and loaded onto the nanoclay. Silver-coated nanoclays in particular have excellent antimicrobial properties, and represent a less expensive alternative to the use of colloidal silver solutions. Such nanoparticles made according to the invention are stable and use less silver metal to generate the same surface area as solid silver particles, making them more cost efficient.

SUMMARY OF THE INVENTION

The present invention relates to a soft surface coating comprising: 1) a composite material comprising (a) an exfoliated nanoparticle having a surface and (b) a metal selected from Groups 3 to 12, aluminum and magnesium, wherein the metal is loaded onto the surface of the nanoparticle; 2) a carrier medium; 3) a surfactant; and 4) one or more adjunct ingredients.

The invention also relates to an absorbent article comprising a composite material comprising (a) an exfoliated nanoparticle having a surface and (b) a metal selected from Groups 3 to 12, aluminum and magnesium, wherein the metal is loaded onto the surface of the nanoparticle.

The invention further relates to a method of modifying a soft surface, which comprises applying thereto a soft surface coating comprising: 1) a composite material comprising (a) an exfoliated nanoparticle having a surface and (b) a metal selected from Groups 3 to 12, aluminum and magnesium, wherein the metal is loaded onto the surface of the nanoparticle; 2) a carrier medium; 3) a surfactant; and 4) one or more adjunct ingredients.

DETAILED DESCRIPTION OF THE INVENTION

Figure 1:
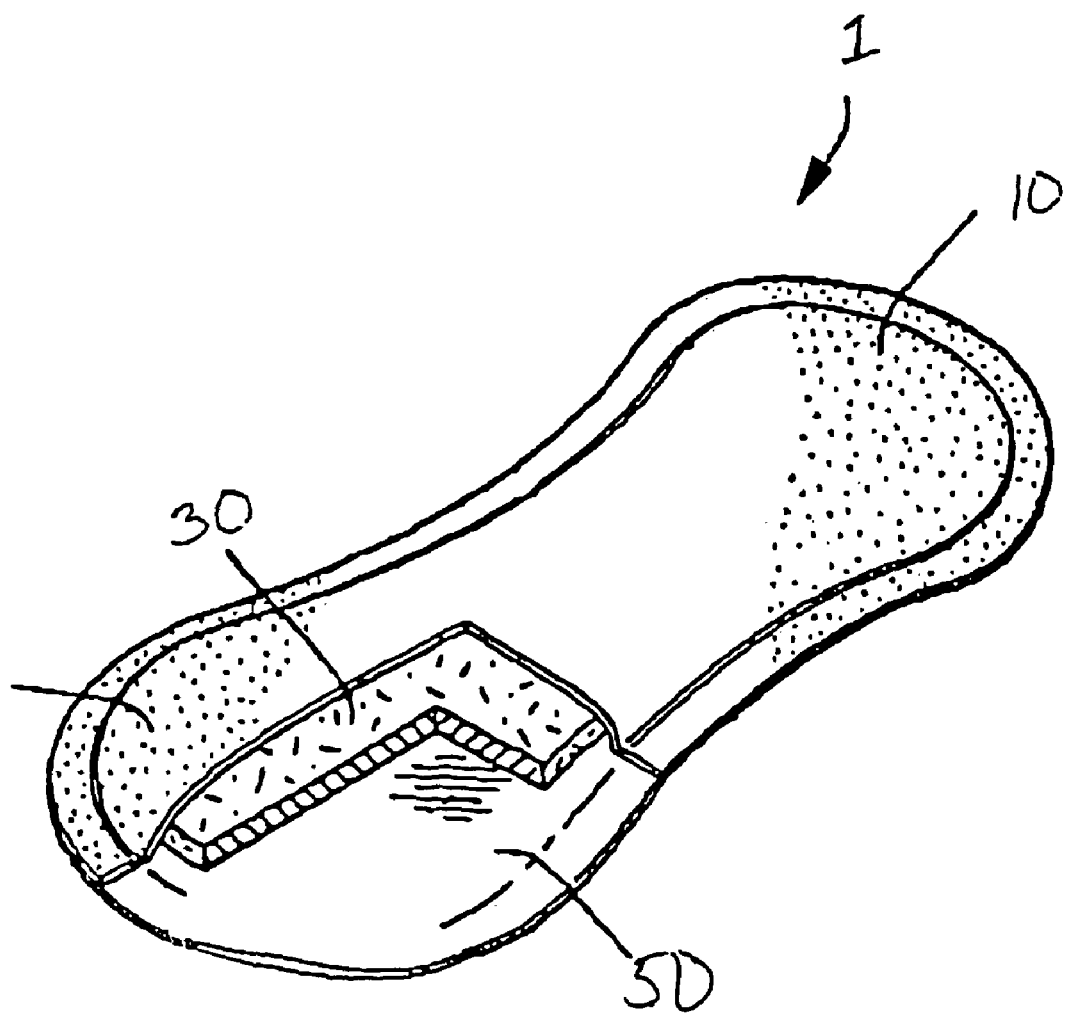
FIG. 1 is a perspective view of an absorbent article according to the present invention.

Every limit given throughout this specification includes every lower or higher limit, as the case may be, as if such lower or higher limit was expressly written herein. Every range given throughout this specification includes every narrower range that falls within such broader range, as if such narrower ranges were all expressly written herein.

According to the invention, absorbent articles may be prepared that comprise a composite material comprising (a) an exfoliated nanoparticle having a surface and (b) a metal selected from Groups 3 to 12, aluminum and magnesium, wherein the metal is loaded onto the surface of the nanoparticle. The composite material may be applied to the absorbent article, for example a layer thereof, in the form of a soft surface coating, as further described herein.

Nanoparticles as used herein means particles (including but not limited to rod-shaped particles, disc-shaped particles, platelet-shaped particles, tetrahedral-shaped particles), fibers, nanotubes, or any other materials having dimensions on the nano scale. In one embodiment, the nanoparticles have an average particle size of about 1 to about 1000 nanometers, preferably 2 to about 750 nanometers. That is, the nanoparticles have a largest dimension (e.g., a diameter or length) of about 1 to 1000 nm. Nanotubes can include structures up to 1 centimeter long, alternatively with a particle size from about 2 to about 50 nanometers. Nanoparticles have very high surface-to-volume ratios. The nanoparticles may be crystalline or amorphous. A single type of nanoparticle may be used, or mixtures of different types of nanoparticles may be used. If a mixture of nanoparticles is used they may be homogeneously or non-homogeneously distributed in the composite material or a system or composition containing the composite material.

Non-limiting examples of suitable particle size distributions of nanoparticles are those within the range of about 2 nm to less than about 750 nm, alternatively from about 2 nm to less than about 200 nm, and alternatively from about 2 nm to less than about 150 nm. It should also be understood that certain particle size distributions may be useful to provide certain benefits, and other ranges of particle size distributions may be useful to provide other benefits (for instance, color enhancement requires a different particle size range than the other properties). The average particle size of a batch of nanoparticles may differ from the particle size distribution of those nanoparticles. For example, a layered synthetic silicate can have an average particle size of about 25 nanometers while its particle size distribution can generally vary between about 10 nm to about 40 nm. It should be understood that the particle size distributions described herein are for nanoparticles when they are dispersed in an aqueous medium and the average particle size is based on the mean of the particle size distribution.

According to the invention, the nanoparticles are exfoliated. In particular, a starting material is exfoliated or disbursed to form the nanoparticles. Such starting material may have an average size of up to about 50 microns (50,000 nanometers). In another embodiment, the nanoparticles are grown to the desired average particle size. The nanoparticle may comprise for example natural or synthetic nanoclays (including those made from amorphous or structured clays), inorganic metal oxides, or nanolatexes.

In one embodiment, the nanoparticle is a nanoclay. In a further embodiment, the nanoparticle is a swellable nanoclay or adduct thereof. A swellable nanoclay has weakly bound ions in interlayer positions that may be hydrated or may absorb organic solvents. These swellable nanoclays generally possess a low cationic or anionic charge, i.e. less than about 0.9 units of charge per unit cell.

As used herein, "adducts" means oil swellable nanoclays, i.e. those that swell in organic, non-aqueous solvents such as polar and nonpolar solvents. They may be prepared by reacting a water swellable nanoclay with an organic material that binds to the swellable nanoclay. Examples of such binding organic materials include, but are not limited to, a quaternary ammonium compound having the structure:

$R_1R_2R_3R_4N+X-$ wherein $R_1$, $R_2$, $R_3$ and $R_4$ are each independently selected from H, a $C_1$ to $C_{22}$ alkyl, a $C_1$ to $C_{22}$ alkenyl, and a $C_1$ to $C_{22}$ aralkyl, provided that at least one of the R groups is such an alkyl, alkenyl or aralkyl; and X is the water swellable nanoclay.

The swellable nanoclay may be amorphous or structured, i.e., including sheets or layers, wherein a combination of such layers is referred to as a lattice structure. Examples of suitable nanoclays having lattice structures include the pyrophillite (dioctahedral) type, the talc (trioctahedral) type, or mixtures thereof. Classes of suitable structured swellable nanoclays include, but are not limited to the smectite nanoclays, sepiolite nanoclays, zeolite nanoclays, palygorskite nanoclays, or mixtures thereof.

Examples of amorphous swellable nanoclays include allophone and imogolite.

In one embodiment, the nanoparticles are made from a starting material such as Nanomer 1.34TCN (available from Nanocor) having a particle size of 10 to 18 microns (10000-18000 nanometers). In another embodiment, the nanoparticles are made from PGV (also available from Nanocor) having a particle size of 20 to 25 microns. In another embodiment, exfoliated PGV having a particle size range of 1-3 nanometers is used. In other embodiments, Nanomer 1.34TCN and Nanomer 1.30E having a particle size range of 1-9 nanometers is used.

Boehmite alumina can have an average particle size distribution from 2 to 750 nm.

Layered clay minerals can be used as starting materials for the exfoliated nanoparticles. The layered clay minerals suitable for use in the present invention include those in the geological classes of the smectites, the kaolins, the illites, the chlorites, the attapulgites and the mixed layer clays. Typical examples of specific clays belonging to these classes are the smectices, kaolins, illites, chlorites, attapulgites and mixed layer clays. Smectites, for example, include montmorillonite, bentonite, pyrophyllite, hectorite, saponite, sauconite, nontronite, talc, beidellite, volchonskoite, stevensite, and vermiculite. In one embodiment, montmorillonite nanoclay is preferred. See U.S. Pat. No. 5,869,033, which is incorporated by reference herein. Kaolins include kaolinite, dickite, nacrite, antigorite, anauxite, halloysite, indellite and chrysotile. Illites include bravaisite, muscovite, paragonite, phlogopite and biotite. Chlorites include corrensite, penninite, donbassite, sudoite, pennine and clinochlore. Attapulgites include sepiolite and polygorskyte. Mixed layer clays include allevardite and vermiculitebiotite. Variants and isomorphic substitutions of these layered clay minerals offer unique applications.

Layered clay minerals may be either naturally occurring or synthetic. For example, natural or synthetic hectorites, montmorillonites and bentonites may be used as the starting material for the nanoparticles.

Natural clay minerals typically exist as layered silicate minerals and less frequently as amorphous minerals. A layered silicate mineral has $SiO_4$ tetrahedral sheets arranged into a two-dimensional network structure. A 2:1 type layered silicate mineral has a laminated structure of several to several tens of silicate sheets having a three layered structure in which a magnesium octahedral sheet or an aluminum octahedral sheet is sandwiched between two sheets of silica tetrahedral sheets.

A sheet of an expandable layer silicate has a negative electric charge, and the electric charge is neutralized by the existence of alkali metal cations and/or alkaline earth metal cations. Smectite or expandable mica can be dispersed in water to form a sol with thixotropic properties. Further, a complex variant of the smectite type clay can be formed by the reaction with various cationic organic or inorganic compounds. An example of such an organic complex, an organophilic clay in which a dimethyldioctadecyl ammonium ion (a quaternary ammonium ion) is introduced by cation exchange. This has been industrially produced and used as a gellant of a coating.

Synthetic nanoclays may be employed in the invention. With appropriate process control, the processes for the production of synthetic nanoclays does indeed yield primary particles that are nanoscale. However, the particles are not usually present in the form of discrete particles, but instead predominantly assume the form of agglomerates due to consolidation of the primary particles. Such agglomerates may reach diameters of several thousand nanometers, such that the desired characteristics associated with the nanoscale nature of the particles cannot be achieved. The particles may be deagglomerated, for example, by grinding as described in EP-A 637,616 or by dispersion in a suitable carrier medium, such as water or water/alcohol and mixtures thereof.

Synthetic materials for making suitable nanoclays include layered hydrous silicate, layered hydrous aluminum silicate, fluorosilicate, mica-montmorillonite, hydrotalcite, lithium magnesium silicate and lithium magnesium fluorosilicate. An example of a substituted variant of lithium magnesium silicate is where the hydroxyl group is partially substituted with fluorine. Lithium and magnesium may also be partially substituted by aluminum. Lithium magnesium silicate may be isomorphically substituted by any member selected from the group consisting of magnesium, aluminum, lithium, iron, chromium, zinc and mixtures thereof.

Synthetic hectorite, for example as commercially marketed under the trade name LAPONITE™ by Southern Clay Products, Inc., may be used as a starting material for the nanoparticles. There are many grades or variants and isomorphous substitutions of LAPONITE™ marketed. Examples of commercial hectorites are LAPONITE B™, LAPONITE S™, LAPONITE XLS™, LAPONITE RD™, LAPONITE XLG™, and LAPONITE RDS™.

Synthetic hectorites do not contain any fluorine. An isomorphous substitution of the hydroxyl group with fluorine will produce synthetic clays referred to as sodium magnesium lithium fluorosilicates, which may also be used as the starting material. These sodium magnesium lithium fluorosilicates, marketed as LAPONITE™ and LAPONITE S™, may contain fluoride ions of up to approximately 10% by weight. The fluoride ion content useful in the compositions described herein is up to about 10 or more percent. LAPONITE B™, a sodium magnesium lithium fluorosilicate, has a flat, circular, plate-like shape, with an average particle size, depending on fluoride ion content, of about 25-100 nanometers. For example, in one non-limiting embodiment, LAPONITE B™ having a diameter of about 25-40 nmand and thickness of about 1 nm may be used. Another variant, called LAPONITE S™, contains about 6% of tetrasodium pyrophosphate as an additive.

In one embodiment, Laponite XLS™ is used as the starting material for the nanoparticle, and silver is loaded thereon as the metal. Laponite XLS has tetrahedral silicate layers joined by octahedral magnesium and lithium hydroxyl bridges. This structure allows for exfoliation and modification by either intercalation or adsorption of metal to the nanoclay surface. In the case of intercalation, the metal is inserted between the layers of nanoclay. In the case of surface adsorption, the metal binds to the surface of the nanoclay. Laponite XLS is advantageous because it is synthetically consistent and pure, and exfoliates to form nanoparticles with minimal effort. The surface of the nanoparticle is covered with sodium ions to balance out the negative charge of the many silicate groups.

The aspect ratio of the exfoliated nanoparticles, in some cases, is of interest in forming films comprising the composite material with desired characteristics. The aspect ratio of dispersions can be adequately characterized by TEM (transmission electron microscopy).

The aspect ratio of nanoparticles in one embodiment can be in the range of 100 to 250. In another embodiment, the aspect ratio of the nanoparticles is 200 to 350.

For example, the average aspect ratio of individual particles of LAPONITE B™ is approximately 20-40 and the average aspect ratio of individual particles of LAPONITE RD™ is approximately 10-15. LAPONITE B™ occurs in dispersions as essentially single clay particles or stacks of two clay particles. LAPONITE RD™ occurs essentially as stacks of two or more single clay particles.

In some embodiments, a high aspect ratio may be desirable for film formation. The aspect ratio of exfoliated nanoparticles dispersed in a suitable carrier medium, such as water, is also of interest. The aspect ratio of the nanoparticles in a dispersed medium is lower where several of the particles are aggregated.

In certain embodiments, it may be desirable for at least some individual (non-aggregated) platelet and disc-shaped nanoparticles to have at least one dimension that is greater than or equal to about 0.5 nm, and an aspect ratio of greater than or equal to about 15. Larger aspect ratios may be more desirable for platelet and disc-shaped nanoparticles than for rod-shaped nanoparticles.

The aspect ratio of rod-shaped nanoparticles can be lower than that of disc-shaped or platelet-shaped nanoparticles while maintaining adequate film-forming properties. In certain non-limiting embodiments, it may be desirable for at least some of the individual rod-shaped nanoparticles to have at least one dimension that is greater than or equal to about 0.5 nm, and an aspect ratio of greater than or equal to about 3.

The aspect ratio of spheroid-shaped nanoparticles is generally less than or equal to about 5. Nanoparticles preferred for the embodiments presented here have aspect ratios of less than or equal to about 250. In other non-limiting embodiments, it may be desirable for the nanoparticles to have an aspect ratio of less than about 10.

According to the invention, one or more metals are used to functionalize the nanoparticle. In particular, they are loaded onto the exfoliated nanoparticle by one of a variety of methods including intercalation, adsorption, or ion exchange. Advantageously, the metal retains its valuable properties, for example in the case of silver its anti-microbial properties, while on the nanoparticle. The term loaded, as used herein, includes complete coverage of the surface of the nanoparticle, or alternatively, only a portion thereof.

In one embodiment, the metal is selected from Groups 3 to 12 of the Periodic Table of Elements, aluminum, and magnesium. Preferably, the metal is selected from silver, copper, zinc, manganese, platinum, palladium, gold, calcium, barium, aluminum, iron, and mixtures thereof. In a particularly preferred embodiment, the metal is silver.

The metal or metals may be selected based on the desired effect to be achieved through use of the composite material. For example, silver may be selected for its known anti-microbial properties.

The metal may be loaded onto the nanoparticle via intercalation. For example, silver ions, in particular, can be inserted among the various layers of layered nanoclay by positioning in a "hole" to maximize favorable interactions between the positively charged silver ion and the various types of oxygen in the silicate structure. Silver ions have been shown to have anti-microbial properties and Laponite that contains intercalated ionic silver, retains these properties. Intercalation is also possible with other metal ions, such as copper, zinc, manganese, etc.

The metal may also be loaded onto the nanoparticle via ion exchange. For example, the surface of Laponite platelets is composed mainly of sodium ions, which exist to balance out the negatively charged oxygen atoms donated by the silicate structure in the layer below. When positively charged metal ions are added to a solution of exfoliated Laponite, a fraction of the surface sodium ions are displaced by the added metal cations.

The metal may also be loaded onto the nanoparticle by adsorption. For example, certain functional groups such as amine, ammonium, and carboxyl groups are strong binders to the face or edge of a platelet of Laponite. Metal ions can be modified by the addition of these ligands so that they are able to bind strongly to the surface of Laponite. The reaction sequence for one example is shown below:

$$2AgNO_3 + 2NaOH \rightarrow Ag_2O + 2NaNO_3 + H_2O$$

$$Ag_2O + 4NH_3 + H_2O \rightarrow 2Ag(NH_3)_2OH$$

The final product, $Ag(NH_3)_2OH$, is contacted with Laponite, whereby the $Ag(NH_3)_2OH$ binds to the face of the Laponite.

In one embodiment of the invention a metal ion is reduced to a metal (0) in the presence of a starting material, which is exfoliated to form a nanoparticle. Reduction and exfoliation may take place in sequence (either step happening first) or simultaneously upon contacting of the metal with the starting material/exfoliated nanoparticle. The metal is thereby loaded onto the surface of the exfoliated nanoparticle.

In one embodiment of the invention, the metal is silver, which is loaded onto the nanoparticle via intercalation using the Tollen's reagent. The Tollen's reagent is a known silver species able to undergo reduction by either an aldehyde or ketone to form silver metal (0):

$$+Ag(NH_3)_2OH + glucose \rightarrow Ag^0$$

The composite material may be incorporated into soft surface coating compositions. Such compositions may be solutions or dry materials, that are coated, applied, extruded, sprayed, and so forth as further described below. Such compositions may have end uses in manufacturing, commercial, industrial, personal, or domestic applications. Use of such coatings containing the composite material can be employed to bring about certain, desired benefits, for example improved fluid absorbency, wettability, strike-through, comfort, malodor control, lubricity, anti-inflammatory properties, antimicrobial properties, anti-fungal properties, modification of surface friction, flexibility, transparency, modulus, tensile strength, color enhancement, viscosity, smoothness, or gel strength.

In certain embodiments, the presence of the composite material in the composition does not affect the desirable properties of the composition, for example transparency. Addition of the composite material to a liquid composition, for instance, will not alter the transparency or color of the resultant composition as compared to the original, liquid material not containing the composite material. Moreover, since nanoparticles possess large surface areas, the composite material will also allow for higher concentrations of metals to be included in the overall formulation, such as in the treatment of infections.

The term "coating", as used herein, includes coatings that completely cover a surface, (e.g., continuous coatings, including those that form films on the surface), as well as coatings that may only partially cover a surface, such as those coatings that after drying leave gaps in coverage on a surface (e.g., discontinuous coatings). The later category of coatings may include, but is not limited to a network of covered and uncovered portions and distributions of composite material on a surface which may have spaces between the composite material. In some embodiments, the coating preferably forms at least one layer of composite material on the surface which has been coated, and is substantially uniform. However, when the coatings described herein are described as being applied to a surface, it is understood that the coatings need not be applied to, or that they cover the entire surface. For instance, the coatings will be considered as being applied to a surface even if they are only applied to modify a portion of the surface.

Soft surface coating compositions of the invention may comprise the composite material and any other ingredients appropriate for the intended use of the compositions. Some compositions of the invention may comprise: (a) the composite material, which may be an effective amount of the composite material; (b) a suitable carrier medium; and (c) optionally one or more adjunct ingredients. The adjunct ingredients may be, for example, surfactants or charged functionalized molecules exhibiting properties selected from the group consisting of hydrophilic, hydrophobic and mixtures thereof associated with at least some of the composite material, or both.

Alternatively, an effective amount of composite material described above can be included in compositions useful for coating a variety of soft surfaces in need of treatment. As used herein, an effective amount of composite material refers to the quantity of composite material necessary to impart the desired benefit to the soft surface. Such effective amounts are readily ascertained by one of ordinary skill in the art and is based on many factors, such as the particular composite material used, the nature of the soft surface whether a liquid or dry (e.g., granular, powder) composition is required, and the like.

The composition may be applied to the surface(s) by washing, spraying, dipping, painting, wiping, or by other manner in order to deliver a coating, especially a transparent coating that covers at least about 0.5% of the surface, or any greater percentage of the surface, including but not limited to: at least about 5%, at least about 10%, at least about 30%, at least about 50%, at least about 80%, and at least about 100% of the surface. Accordingly, the coating may be continuous or discontinuous.

If the coating composition is to be sprayed onto the surface, the viscosity of the coating composition should be such that it will be capable of passing through the nozzle of a spray device. Such viscosities are well known, and are incorporated herein by reference. The composition may be capable of undergoing shear thinning so that it is capable of being sprayed.

Suitable carrier mediums for the compositions containing the composite material include liquids, solids and gases. One suitable carrier medium is water, which can be distilled, deionized, or tap water. Water is valuable due to its low cost, availability, safety, and compatibility. The pH of the liquid, in particular water, may be adjusted through the addition of acid or base. Aqueous carrier mediums are also easy apply to a substrate and then dried. Though aqueous carrier mediums are more common than dry, nonaqueous mediums, the composition can exist as a dry powder, granule or tablet or encapsulated complex form.

Optionally, in addition to or in place of water, the carrier medium can comprise a low molecular weight organic solvent. Preferably, the solvent is highly soluble in water, e.g., ethanol, methanol, propanol, isopropanol, ethylene glycol, acetone, and the like, and mixtures thereof. The solvent can be used at any suitable level. Several non-limiting examples, include a level of up to about 50%, or more; from about 0.1% to about 25%; from about 2% to about 15%, and from about 5% to about 10%, by weight of the total composition. Factors to consider when a high level of solvent is used in the composition are odor, flammability, dispersancy of the nanoparticles and environmental impact.

The carrier medium may also comprise a film former, which when dried, forms a continuous film. Examples of film formers are polyvinyl alcohol, polyethylene oxide, polypropylene oxide, acrylic emulsions, hydroxypropylmethyl cellulose.

Adjunct ingredients that may be used in compositions containing the composite material include polymers and copolymers with at least one segment or group which comprises functionality that serves to anchor the composite material to a substrate. These polymers may also comprise at least one segment or group that serves to provide additional character to the polymer, such as hydrophilic or hydrophobic properties.

Examples of the anchoring segments or groups include: polyamines, quaternized polyamines, amino groups, quaternized amino groups, and corresponding amine oxides; zwitterionic polymers; polycarboxylates; polyethers; polyhydroxylated polymers; polyphosphonates and polyphosphates; and polymeric chelants.

Examples of the hydrophilizing segments or groups include: ethoxylated or alkoxylated polyamines; polyamines; polycarboxylated polyamines; water soluble polyethers; water soluble polyhydroxylated groups or polymers, including saccharides and polysaccharides; water soluble carboxylates and polycarboxylates; water soluble anionic groups such as carboxylates, sulfonates, sulfates, phosphates, phosphonates and polymers thereof; water soluble amines, quaternaries, amine oxides and polymers thereof; water soluble zwitterionic groups and polymers thereof; water soluble amides and polyamides; and water soluble polymers and copolymers of vinylimidazole and vinylpyrrolidone.

Examples of the hydrophobizing segments or groups include: alkyl, alkylene, and aryl groups, and polymeric aliphatic or aromatic hydrocarbons; fluorocarbons and polymers comprising fluorocarbons; silicones; hydrophobic polyethers such as poly(styrene oxide), poly(propylene oxide), poly(butylene oxide), poly(tetramethylene oxide), and poly(dodecyl glycidyl ether); and hydrophobic polyesters such as polycaprolactone and poly(3-hydroxycarboxylic acids). Examples of hydrophilic surface polymers that may be incorporated into the compositions of the invention include, but are not limited to: ethoxylated or alkoxylated polyamines; polycarboxylated polyamines; polycarboxylates including but not limited to polyacrylate; polyethers; polyhydroxyl materials; polyphosphates and phosphonates.

Examples of hydrophobic surface polymers that may be incorporated into the compositions of the invention include alkylated polyamines include, but are not limited to: polyethyleneimine alkylated with fatty alkylating agents such as dodecyl bromide, octadecyl bromide, oleyl chloride, dodecyl glycidyl ether and benzyl chloride or mixtures thereof; and polyethyleneimine acylated with fatty acylating agents such as methyl dodecanoate and oleoyl chloride; silicones including, but not limited to: polydimethylsiloxane having pendant aminopropyl or aminoethylaminopropyl groups and fluorinated polymers including, but not limited to: polymers including as monomers (meth)acrylate esters of perfluorinated or highly fluorinated alkyl groups.

Non-polymeric surface modifying materials that may be used as adjunct ingredients include fatty amines and quaternized amines including: ditallowdimethylammonium chloride; octadecyltrimethylammonium bromide; dioleyl amine; and benzyltetradecyldimethylammonium chloride. Silicone-based surfactants, fatty zwitterionic surfactants and fatty amine oxides may also be incorporated into the coating composition.

Surfactants are also optional adjunct ingredients. Surfactants are especially useful in the composition as wetting agents to facilitate the dispersion.

Suitable surfactants can be selected from the group including anionic surfactants, cationic surfactants, nonionic surfactants, amphoteric surfactants, ampholytic surfactants, zwitterionic surfactants and mixtures thereof. Examples of suitable nonionic, anionic, cationic, ampholytic, zwitterionic and semi-polar nonionic surfactants are disclosed in U.S. Pat. Nos. 5,707,950 and 5,576,282. Nonionic surfactants may be characterized by an HLB (hydrophilic-lipophilic balance) of from 5 to 20, alternatively from 6 to 15.

Mixtures of anionic and nonionic surfactants are especially useful. Other conventional useful surfactants are listed in standard texts.

Another class of adjunct ingredients that may be useful is silicone surfactants and/or silicones. They can be used alone and/or alternatively in combination with other surfactants described herein above. Nonlimiting examples of silicone surfactants are the polyalkylene oxide polysiloxanes having a dimethyl polysiloxane hydrophobic moiety and one or more hydrophilic polyalkylene side chains.

If used, the surfactant should be formulated to be compatible with the composite material, carrier medium and other adjunct ingredients present in the composition.

The soft surface coating compositions can contain other adjunct ingredients, including but not limited to alkalinity sources, antioxidants, anti-static agents, chelating agents, aminocarboxylate chelators, metallic salts, photoactive inorganic metal oxides, odor-controlling materials, perfumes, photoactivators, polymers, preservatives, processing aids, pigments, and pH control agents, solubilizing agents, zeolites, and mixtures thereof. These optional ingredients may be included at any desired level.

Coating compositions comprising the composite material can be used on all types of soft surfaces, including but not limited to woven fibers, nonwoven fibers, leather, plastic (for example, toothbrush handles, synthetic film, filaments, toothbrush bristles), and mixtures thereof. The soft surfaces of interest herein may comprise any known type of soft surface, including but not limited to those associated with disposable absorbent articles including but not limited to covers or topsheets, absorbent cores, transfer layers, absorbent inserts, and backsheets including those outer layers made from breathable and nonbreathable films.

In certain embodiments, the soft surface may comprise one or more fibers. A fiber is defined as a fine hairlike structure, of vegetable, mineral, or synthetic origin. Commercially available fibers have diameters ranging from less than about 0.001 mm (about 0.00004 in) to more than about 0.2 mm (about 0.008 in) and they come in several different forms: short fibers (known as staple, or chopped), continuous single fibers (filaments or monofilaments), untwisted bundles of continuous filaments (tow), and twisted bundles of continuous filaments (yarn). Fibers are classified according to their origin, chemical structure, or both. They can be braided into ropes and cordage, made into felts (also called nonwovens or nonwoven fabrics), woven or knitted into textile fabrics, or, in the case of high-strength fibers, used as reinforcements in composites-that is, products made of two or more different materials.

The soft surfaces may comprise fibers made by nature (natural fibers), made by man (synthetic or man-made), or combinations thereof. Example of natural fibers include but are not limited to: animal fibers such as wool, silk, fur, and hair; vegetable fibers such as cellulose, cotton, flax, linen, and hemp; and certain naturally occurring mineral fibers. Synthetic fibers can be derived from natural fibers or not. Examples of synthetic fibers which are derived from natural fibers include but are not limited to rayon and lyocell, both of which are derived from cellulose, a natural polysaccharide fiber. Synthetic fibers which are not derived from natural fibers can be derived from other natural sources or from mineral sources. Examples of synthetic fibers derived from natural sources include but are not limited to polysaccharides such as starch. Example fibers from mineral sources include but are not limited to polyolefin fibers such as polypropylene and polyethylene fibers, which are derived from petroleum, and silicate fibers such as glass and asbestos. Synthetic fibers are commonly formed, when possible, by fluid handling processes (e.g., extruding, drawing, or spinning a fluid such as a resin or a solution). Synthetic fibers are also formed by solid handling size reduction processes (e.g., mechanical chopping or cutting of a larger object such as a monolith, a film, or a fabric).

Disposable absorbent articles, such as pantiliners, sanitary napkins, interlabial devices, adult incontinent devices, breast pads, shoe insoles, bandages, and diapers typically are made from absorbent, nonwoven materials (including fibers) and are well known in the art. These articles typically have a fluid permeable body-facing side and fluid impermeable garment facing side. Additionally, such articles may include an absorbent core for retaining fluids therebetween. Addition of the composite material to an article of manufacture such as the absorbent core of a disposable, absorbent article may help control malodor formation and increase absorbency.

FIG. 1 depicts an absorbent article according to the invention. Although not required, the absorbent article 1 may include a cover 10 overlaying the absorbent core 30. The exterior of the cover would then form the body-facing surface of the absorbent article. As known by those skilled in the art, the cover may be formed from any fluid pervious material that is generally compliant, soft feeling, and non-irritating to the user's skin and permits fluid to penetrate to the absorbent core, which retains the fluid. The cover generally functions to transport fluid away from the wearer into the absorbent article. In this manner, fluid and moisture are removed from contacting the wearer, thus making the wearer feel dry and comfortable. In addition to transporting fluid, the cover may also absorb and/or retain fluid as well.

The cover can be made from any of the materials conventional for this type of use. Non-limiting examples of suitable materials that can be used as the cover are woven and nonwoven fabrics formed from cellulose, polyester, polypropylene, nylon, and/or rayon fibers or the cover layer may be an apertured thermo-plastic film and formed films. Other materials used in making covers include gauze or any known porous material with a suitable body contacting surface, including, but not limited to nonwoven webs, plastic nets, and the like. The cover could also be made from a fibrous nonwoven composite of bicomponent fibers and pulp fluff.

Bicomponent fibers are known in the art and are composed of two polymers with different melting points. At least a portion of the outer surface of each bicomponent fiber has the lower melting polymer. The two polymers may be arranged such that a cross-section of the fiber shows the two polymers in a side-by-side array. Alternatively, the polymers may be positioned in a so-called sheath/core arrangement, in which a core of higher melting polymer is surrounded by a sheath of lower melting polymer. A useful bicomponent fiber is a 3.0 denier, 1.5" long staple fiber made of a polyester core and a high density polyethylene sheath. Similar fibers (polyethylene sheath and polypropylene core) are available as Danaklon ES-C or ES Bico (Danaklon A/S, Varde Denmark). Pulp fibers may be obtained as IP "SUPERSOFT" ELM supplied by the International Paper Company (Memphis, Tenn.), "RAYFLOC" XJ-HM E-Type Cellulosic Fluff Pulp, (ITT Rayonier), or Korsnas Vigorfluf-EN White (KorsncAs, Gavle, Finland).

The cover may optionally be treated with surfactant to manipulate the hydrophobicity/hydrophilicty thereof to facilitate optimal fluid transport properties. The fibers or other materials that make up the cover layer should not collapse or lose their resiliency when subjected to body fluid. The fibers may be oriented by a carding process and thermally bonded via embossing. The fiber or filament can be single denier or multidenier.

The thickness of the cover may vary from about 0.025 mm to about 5 mm, depending on the material chosen. The weight of the body-facing layer material should be between about 5 to about 150 grams per square meter (gsm).

Generally, the optional cover is a single sheet of material having a width sufficient to form the body-facing surface of the absorbent article. The cover may be longer and wider than the absorbent core.

The cover may be embossed with shapes within a given area. For example, a series or a number of features, e.g., circles, triangles, squares, lines, honeycomb, diamond, floral, etc., are embossed over the entire length and width of the outer surface of web. Each embossed feature has a major and minor axis extending therethrough, the major axis length being greater or equal to the minor axis length. The embossed features may be in a repetitive pattern.

In one embodiment of the invention, the cover includes a spunlace nonwoven. In particular, the spunlace material may be made from about 0 to about 100% rayon and from about 0 to about 100% polyester. The spunlace material may also be made from about 10 to about 65% rayon and from about 35 to about 90% polyester may be used. Optionally, the material used for the body-facing layer may include binders, such as, thermoplastic binder fibers and latex binders.

Optionally, the absorbent article of the present invention may include a transfer or distribution layer (not shown). The transfer layer or distribution layer, if present, is generally positioned beneath the cover 10 and the transfer layer usually directly contacts the absorbent core. If included, the transfer layer may be made of any known material that will take up fluid and then distribute and release it to an adjacent absorbent layer for storage. Transfer layers have a relatively open structure that allows for movement of fluid within the layer. Suitable materials for such transfer layers include fibrous webs, resilient foams, and the like.

The transfer layer provides a means of receiving body fluid from the fluid-pervious cover and holding it until the absorbent core has an opportunity to absorb it. The transfer layer is, preferably, more dense than the cover and has a larger proportion of smaller pores than does the cover. These attributes allow the transfer layer to contain body fluid and hold it away from the outer side of the cover layer 10, thereby preventing the fluid from re-wetting the cover and its outer surface. However, the transfer layer is preferably not so dense as to prevent the passage of the fluid through the transfer layer and into the underlying absorbent core.

The transfer layer may include various materials, including, for example, fibrous webs, resilient foams, and the like. The transfer layer may include cellulose fibers such as from wood pulp, single component or bicomponent fibers that include thermoplastic materials (such as, polyester, polypropylene, polyethylene, among others) in fiber or other forms, rayon, organic binders (such as, copolymers of vinyl, acrylic and/or other monomers that may be coated onto thermoplastic fibers or otherwise incorporated into the transfer layer) among other materials known to the art. The transfer layer may, for example, have a basis weight in a range from about 40 gsm to about 120 gsm, a thickness in a range from about 0.5 mm to about 4 mm, a density in a range from about 0.03 g/cc to about 0.15 g/cc.

The mass of materials making up the transfer layer may be absorbent, although the materials themselves are not absorbent. Thus, transfer layers that are made of hydrophobic, nonabsorbent fibers may be able to accept large volumes of fluid into interfiber void spaces while the fibers themselves do not absorb any significant quantities of fluid. Likewise, open-celled foam structures that are made from nonabsorbent materials may also absorb fluid into the cells of the foam. The walls of the cells, however, do not absorb any fluid. The cumulative spaces within the transfer layer, i.e., the interfiber void spaces in the fibrous transfer layer or the open cells in the foam transfer layer, function much like a container to hold fluid.

Typically, transfer layer fibrous webs are made of resilient, nonabsorbent materials to provide void volume and to allow for free movement of fluid through the structure. Transfer layers that are made from webs of mostly absorbent fibers absorb the fluid as it enters the structure and do not distribute it throughout the rest of the structure as efficiently as webs containing non-absorbent materials.

Transfer layers that are made from webs of mostly absorbent fibers absorb the fluid as it enters the structure and do not distribute it throughout the rest of the structure as efficiently as webs containing non-absorbent materials. Preferred transfer-layer fibrous webs include nonabsorbent materials to provide void volume and to allow for free movement of fluid through the structure. Examples of such materials include polypropylene, polyethylene, polyester, bicomponent materials, nylon and mixtures or combinations thereof. The transfer layer does not have to be apertured film; it can be any other nonwoven material, such as, foam or netting, which transports fluid and, in combination with the cover, provides masking of the absorbent core. However, in one embodiment, the transfer layer is a 25 gsm apertured film made from polyethylene. Coat fibers, also—cover, transfer, core.

Absorbent core 30 may be made from any known absorbent materials including, but not limited to, absorbent fibers, such as, cellulose fibers, including, but not limited to wood pulp, regenerated cellulose fibers, and cotton fibers, rayon fibers and the like; superabsorbent powders (SAP) like Sumitomo SA-70 or fibers (SAF), other naturally occurring absorbent materials, such as, sphagnum or peat moss; and other synthetic absorbent materials, such as, foams and the like. The absorbent core 30 may also include one or more of the following: binders, such as, thermoplastic and latex, odor-controlling compounds, e.g., perfumes, EDTA (ethylenediaminetetraacetic acid), anti-microbial agents, wetting agents, wetness indicator material, materials for administering or delivering medicaments, such as encapsulated medicaments, and materials for maintaining skin moisture, such as encapsulated moisturizers.

For example, the absorbent core may be made from material such as a fluffy batt cut from a relatively loose web of non-woven fibers having a relatively high absorptive capacity. While the absorbent core can have any shape or silhouette, it usually has an asymmetric configuration. The absorbent core 30 may also be made from material such as a fibrous batt having an integral densified layer. In such a case, if a backsheet is desired, the absorbent core is positioned on the backsheet of the absorbent article so that the densified layer adjoins the backsheet. The densified layer has relatively higher wettability and liquid retentivity than the rest of the aforesaid batt and usually is formed by slightly moistening one surface of the batt and thereafter compressing the moistened surface. The absorbent core 30 may also be formed from multiple layers, each having a different density such that the uppermost layer (closest to the body) is less dense than the outer (closest to the garment).

Additionally, the absorbent core may be formed of absorbent material made from an offline-formed, homogeneously mixed, air-laid layer, roll good laminate or any other offline-formed absorbent composite.

The absorbent material of this invention may be made from a number of processes, including, but not limited to, airlaying, spunbonding, bonding and carding, meltblowing, and coforming. In one embodiment, the absorbent core is absorbent core air-laid pulp.

The airlaid process is well known. A fibrous nonwoven composite made from Buckeye Foley Fluff™ (Memphis, Tenn.) pulp, Trevira or KoSa T255 (Houston, Tex.) bicomponent fibers can be formed by the separation of bundles of short fibers entrained into an air stream. These fibers are deposited onto a forming screen, typically a horizontal or rotary drum, with the aid of a vacuum supply. There may be multiple forming sections (forming heads). The random web is bonded together via a hot-air activated latex-bonding adhesive, thermal bonding fibers, or combination, as taught in, for example, U.S. Pat. Nos. 4,640,810 and 5,885,516.

The binder may be in the form of fibers, liquid or particles. Binders may aid in preventing wet collapse of the material. Suitable fiber binders that can be used with this invention include sheath core conjugate fibers available from KoSa Inc. (Houston, Tex.) under the designation T-255 and T-256, both with a polyolefin sheath, or T-254, which has a low-melt co-polyester sheath. Other fiber binders are known to those skilled in the art, and are available by many manufacturers such as Chisso and Fibervisions LLC of Wilmington, Del. A suitable liquid binder is KYMENE® 557LX available from Hercules, Inc. of Wilmington, Del. Other suitable liquid binders include ethylene vinyl acetate emulsion polymers sold by National Starch and Chemical Company (Bridgewater, N.J.) under the tradename DUR-O-SET® ELITE a series (including ELITE® 33 and ELITE® 22). Other suitable binders are sold by Air Products Polymers and Chemicals under the name AIRFLEX®.

Some binders require catalysts, elevated temperatures, and/or acidic conditions in order to cross-link. Monomers derived from the reaction of a polymerizable amide with an aldehyde are conventionally used for such purposes. The binder can be applied to the top, bottom, or both of the layers at various add on levels. Different types of latex binders, e.g., high Tg, e.g., about +10 to about +35° C., or low Tg, e.g, about −3 to about −30° C., those binders having Tg between the high and low have differing degrees of stiffness and softness and may be applied independently or, in combination, depending on the desired properties of the resulting structure. See for example, U.S. Pat. Nos. 4,449,978 and 5,143,954. Other binders such as those disclosed in U.S. Pat. No. 5,415,926, the entire disclosure incorporated herein in its entirety, are considered to be self-crosslinking. In these polymer systems, a reactive functional group allows the polymer to cross link with itself, as well as chemically bond to the substrate such as pulp or tissue. The self-crosslinking reaction can be accelerated through the use of acid catalysts. An example of a self-crosslinking binder includes "X-LINK 25-033A", a self-crosslinking vinyl acrylic copolymer emulsion having a high glass transition temperature, available from National Starch and Chemical Company (Bridgewater, N.J.).

The absorbent material may also be deposited onto a carrier substrate, e.g., tissue (not shown) or other air permeable composition to form an absorbent structure. In this configuration, the layers are typically sprayed with a binder to stabilize the resulting absorbent structure. The structure can further be pattern embossed to achieve aesthetics and/or functionality, e.g., wicking, densification, and the like. The resulting structure can be used as an absorbent structure into absorbent products, such as, sanitary napkins or pantiliners.

In one embodiment, the absorbent structure contains an absorbent core made from absorbent material and a tissue layer. In one embodiment, the tissue layer is placed between the absorbent material and barrier layer 50. The tissue layer may be made from softwood and/or hardwood fibers and can be creped, wet pressed, or through-air dried.

Other additives may be incorporated into the absorbent core, such as, surfactants, SAP, and SAF. These additives may provide additional benefits such as enhanced fluid penetration and increased fluid absorption. For example, in one embodiment, the absorbent layer is made of absorbent material that is made from a layer of pulp. In another embodiment, SAP is mixed with the pulp to form an absorbent composite. This composite may be condensed to form a dense, thin layer. One example of such a material is Novathin® available from Rayonier, Jessup, Ga.

SAP are particles that are capable of absorbing many times, at least 10, more preferably 15, and still more preferably over 15, their weight in exudate, under a pressure of 0.5 psi. It should be noted that, in the context of the present invention, there is no restriction that the superabsorbent particles actually be particulate. This expression is intended to cover superabsorbent fibers, and other superabsorbent materials, whatever their form and shape. These superabsorbent particles generally fall into three classes, namely starch graft copolymers, cross-linked carboxymethylcellulose derivates and modified hydrophilic polyacrylates. Examples of such absorbent polymers are hydrolyzed starch-acrylonitrile copolymer graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-cross-linking polyacrylic acid, a cross-linked polyacrylate salt, carboxylated cellulose, and a neutralized cross-linked isobutylene-malasic anhydride copolymer. In one embodiment of the invention, the superabsorbent particle is a cross-linked polyacrylate salt.

The superabsorbent particles are incorporated into the absorbent core in an amount no greater than about 60% on a weight per weight basis. Preferably, they are incorporated in an amount between about 0% and about 25% on a weight per weight basis. More preferably, they are incorporated in an amount between about 5% and about 20% on a weight per weight basis. For example, in the present context, 7% superabsorbent on "a weight per weight basis" is meant to mean 0.07 grams of superabsorbent particles per 1 gram of all components in the absorbent core.

The absorbent layer or core of the present invention may be constructed according to conventional techniques, e.g., by air-laying a mixture of wood pulp fibers and superabsorbent material. All such conventional techniques are within the scope of the present invention. In one embodiment, an absorbent layer is as described in U.S. Pat. No. 5,866,242, which is herein incorporated by reference in its entirety.

The ratio of SAP to wood pulp may be varied over a wide range. If desired, a layer or multilayer of drylaid-type material can be used as the absorbent material to form the absorbent core. The absorbent material may be made of a SAP of the type used in the art and wood pulp fibers having the desired density.

Any tissue known in the art may be used to produce an absorbent structure of the present invention, e.g., air-laid tissue and a wet-laid tissue.

The barrier layer, also called backsheet 50, may be located adjacent to the absorbent core 30 and to the cover 10 in portions elsewhere. The barrier layer 50 of the present invention is a body fluid impervious material, which is at least substantially impermeable to liquids. Its exterior forms the garment-facing surface of the absorbent article. The backsheet 50 may be any thin, flexible, body-fluid impermeable material, such as, but not limited to, a polymeric film, e.g., polyethylene, polypropylene, or cellophane, or a normally fluid pervious material that has been treated to be impervious, such as impregnated fluid repellent paper or non-woven material, including nonwoven fabric material, or a flexible foam, such as polyurethane or cross-linked polyethylene.

Optionally, the backsheet 50 may be breathable, i.e., permits vapor to transpire. Known materials for this purpose include nonwoven materials, monolithic and microporous films in which microporosity is created by, inter alia, stretching an oriented film. Single or multiple layers of permeable films, fabrics, melt-blown materials, and combinations thereof that provide a tortuous path, and/or whose surface characteristics provide a liquid surface repellent to the penetration of liquids may also be used to provide a breathable backsheet.

The layers of the absorbent article may be, but not necessarily, bonded, e.g., glued or adhered, to the adjacent layer. For example, the underside of the cover 10 may be adhered to the topside of the absorbent core 30. The underside of the absorbent core 30 may be adhered to the topside of the barrier layer 50. Any methods known in the art, such as, fusion bonding, adhesive attachment, or by any other securement means can be used to secure the individual layers together to form the final absorbent article. Included within such methods are coembossing, thermobonding, mechanical bonding, and the like. Fusion bonding includes heat bonding, ultrasonic bonding, and the like.

Adhesive is typically used to attach the layers into a single absorbent article. For example, in one embodiment, the body facing cover 10 is attached to the barrier layer 50 with adhesive HL 1491 available from H.B Fuller and Company (St. Paul, Minn.). The adhesive may be applied in any method.

Adhesive may include pressure sensitive adhesive that is applied as strips, swirls, or waves, and the like. As used herein, the term pressure-sensitive adhesive refers to any releasable adhesive or releasable tenacious means. Suitable adhesive compositions, include, for example, water-based pressure-sensitive adhesives such as acrylate adhesives. Alternatively, the adhesive composition may include adhesives based on the following: emulsion or solvent-borne adhesives of natural or synthetic polyisoprene, styrene-butadiene, or polyacrylate, vinyl acetate copolymer or combinations thereof; hot melt adhesives based on suitable block copoylmers—suitable block copolymers for use in the invention include linear or radial co-polymer structures having the formula (A-B)x wherein block A is a polyvinylarene block, block B is a poly(monoalkenyl) block, x denotes the number of polymeric arms, and wherein x is an integer greater than or equal to one. Suitable block A polyvinylarenes include, but are not limited to, Polystyrene, Polyalpha-methylstyrene, Polyvinyltoluene, and combinations thereof. Suitable Block B poly(monoalkenyl) blocks include, but are not limited to, conjugated diene elastomers such as, for example, polybutadiene or polyisoprene or hydrogenated elastomers such as ethylene butylene or ethylene propylene or polyisobutylene, or combinations thereof. Commercial examples of these types of block copolymers include Kraton™ elastomers from Shell Chemical Company, Vector™ elastomers from Dexco, Solprene™ from Enichem Elastomers and Stereon™ from Firestone Tire & Rubber Co.; hot melt adhesive based on olefin polymers and copolymers where in the olefin polymer is a terpolymer of ethylene and a comonomer, such as vinyl acetate, acrylic acid, methacrylic acid, ethyl acrylate, methyl acrylate, n-butyl acrylate vinyl silane or maleic anhydride. Commercial examples of these types of polymers include Ateva (polymers from AT plastics), Nucrel (polymers from DuPont), Escor (from Exxon Chemical).

The absorbent article of the present invention may be applied to the crotch of a garment by placing the garment-facing surface against the inside surface of the crotch of the garment. Various methods of attaching absorbent articles may be used. For example, chemical means, e.g., adhesive, and mechanical attachment means, e.g., clips, laces, ties, and interlocking devices, e.g., snaps, buttons, VELCRO (Velcro USA, Inc., Manchester, N.H.), zipper, and the like are examples of the various options available to the artisan.

Adhesive may be applied to the garment-facing side of the absorbent article. The positioning adhesive may be any adhesive known in the art. As a non-limiting example, pressure sensitive adhesive strips, swirls, or waves may be applied to help maintain the absorbent article in place. As used herein, the term pressure-sensitive adhesive refers to any releasable adhesive, or releasable tenacious means. Suitable adhesive compositions, include, for example, water-based pressure-sensitive adhesives, such as acrylate adhesives. Alternatively, the adhesive composition may include rapid setting thermoplastic "hot melt," rubber adhesives, two-sided adhesive tape, and the like.

Where positioning adhesive is used on the garment-facing side of the barrier layer 50, a release strip may be applied to protect the adhesive on the absorbent article prior to attaching the absorbent article to the crotch. The release strip can be formed from any suitable sheet-like material that adheres with sufficient tenacity to the adhesive to remain in place prior to use but which can be readily removed when the absorbent article is to be used. Optionally, a coating may be applied to release strip to improve the ease of removability of the release strip from the adhesive. Any coating capable of achieving this result may be used, e.g., silicone.

Wings, also called, among other things, flaps or tabs, may also be part of the absorbent article of the present invention. Wings and their use in sanitary protection articles are described in U.S. Pat. No. 4,687,478 to Van Tilburg; U.S. Pat. No. 4,589,876 also to Van Tilburg, U.S. Pat. No. 4,900,320 to McCoy, and U.S. Pat. No. 4,608,047 to Mattingly. The disclosures of these patents are incorporated herein by reference in their entirety.

As disclosed in the above documents, wings are, generally speaking, flexible and configured to be folded over the edges of the underwear so that the wings are disposed between the edges of the underwear.

Any or all of the cover, absorbent layer, transfer layer, backsheet layer, and adhesive layers may be transparent or colored. Such coloring includes, but is not limited to, white, black, red, yellow, blue, orange, green, violet, and mixtures thereof. Color may be imparted according the present invention through dying, pigmentation, and printing. Colorants used according the present invention include dyes and inorganic and organic pigments. The dyes include, but are not limited to, anthraquinone dyes (Solvent Red 111, Disperse Violet 1, Solvent Blue 56, and Solvent Green 3), Xanthene dyes (Solvent Green 4, Acid Red 52, Basic Red 1, and Solvent Orange 63), azine dyes (Jet black), and the like.

Inorganic pigments include, but are not limited to, titanium dioxide (white), carbon black (black), iron oxides (red, yellow, and brown), chromium oxide (green), ferric ammonium ferrocyanide (blue), and the like.

Organic pigments include, but are not limited to, diarylide yellow AAOA (Pigment Yellow 12), diarylide yellow AAOT (Pigment Yellow 14), phthalocyanine blue (Pigment Blue 15), lithol red (Pigment Red 49:1), Red Lake C (Pigment Red), and the like.

In one embodiment, the absorbent article has a cover and a backsheet, which are held together by a layer of adhesive. The adhesive layer contains nanoparticles, which absorb body fluids. In another embodiment, the absorbent article has a cover, backsheet, an absorbent portion containing nanoparticles and has a drapeability of less than XX as defined by U.S. Pub. No. 2003114822, filed Dec. 19, 2001.

In another embodiment, the absorbent article is transparent as defined by U.S. Pat. Nos. 6,497,690 and 6,482,192. In this embodiment, the absorbent portion of the article contains nanoparticles such that the resultant article maintains its transparency.

The absorbent article may be packaged as unwrapped absorbent articles within a carton, box or bag. The consumer withdraws the ready-to-use article as needed. The absorbent article may also be individually packaged (each absorbent article encased within an overwrap).

Also contemplated herein include asymmetrical and symmetrical articles having parallel longitudinal edges, dog bone- or peanut-shaped, circular, oval and the like.

An absorbent article of the present invention may be used with conventional underwear or may be shaped to conform to thong garments. As used herein, the term thong includes, but is not limited to, thong underwear, thong swimming suit bottom, G-strings, Rio cut underwear, Rio cut swimming suit bottom, Brazilian cut underwear, Brazilian cut swimming suit bottom, and any other garment that exposes the buttocks, having a narrow strip of fabric or a cord that passes between the thighs supported by a waistband, a waist cord, belt or the garment itself. The absorbent article may include other known materials, layers, and additives, such as, foam, net-like material, perfumes, medicaments or pharmaceutical agents, moisturizers, odor control agents, and the like. The absorbent article can optionally be embossed with decorative designs.

In any of the embodiments of the methods described herein, it may be desirable to perform a step of preparing the soft surface(s) in some suitable manner to enhance the ability of the surface to receive the coating composition.

Hydrophobic or borderline hydrophilic soft surfaces include, but are not limited to, materials such as knitted, woven, and nonwoven materials that are comprised of hydrophobic or borderline hydrophilic structural components. The structural components of a knitted, woven, or nonwoven material may comprise yarns, strands, fibers, threads, or other structural components. Some or all of the structural components may be hydrophobic, borderline hydrophilic, or combinations thereof. Hydrophobic structural components are those that entirely comprise a hydrophobic material, or partially comprise a hydrophobic material on the surface (such as a multi-component fiber comprising a core of one or more materials partially or fully surrounded by a hydrophobic sheath).

Similarly, borderline hydrophilic structural components are those that entirely comprise a borderline hydrophilic material or partially comprise a borderline hydrophilic material on the surface. If a structural component includes both hydrophobic materials and borderline hydrophilic materials on the surface, then it is considered hydrophobic. Hydrophobic materials are often synthetic polymers, co-polymers, blends, or combinations thereof. Examples include, but are not limited to, polyolefins such as polypropylene and polyethylene, and to certain polyesters such as polyethylene terepthalate (PET), and to certain polyamides. Borderline hydrophilic materials are also often synthetic polymers, co-polymers, blends, or combinations thereof. Examples include, but are not limited to, polyamides and polyesters which exhibit borderline hydrophilicity. Polyesters with borderline hydrophilicity include the class of polyesters which have recently been termed hydrophilic polyesters. One example is PET/branched polyethylene glycol (branched PEG) co-polymers such as the T870, T289, and T801 grades available from Wellman, Inc., Charlotte, N.C., USA. Another example is polyesters with aliphatic repeat units instead of some or all of the aromatic repeat units of PET. Polylactide (or polylactic acid or PLA) polymers available from Cargill Dow Polymers, LLC, Blair Nebr. contain aliphatic repeat units.

The ability of the surface to which the coating composition is applied to receive the coating composition can be enhanced in a non-limiting number of different ways.

As discussed herein, one way of enhancing the ability of the surface of the material to receive the coating composition is through the use of surfactants. Surfactants reduce the surface tension of water-based nanoparticle dispersions, thereby improving wettability of the soft surface. Wetting the surface is important because it allows the dispersion to carry the nanoparticles across a greater surface area thereby increasing coverage.

While surfactants may work well for many applications, in the case of some of the hydrophobic or borderline hydrophilic materials described above, presence of residual surfactant from the coating process may be particularly problematic when the material is subsequently rewetted during use, such as in articles which transport fluid including but not limited to absorbent articles and disposable absorbent articles such as diapers and other incontinence and catamenial products such as feminine pads, that are subject to one or more gushes of liquid during use (e.g., urine, menses, sweat, or other body exudates).

Liquid gushes wash the residual surfactant from the soft surface into the liquid phase itself during use. Even low levels of residual surfactant in the liquid phase reduce the surface tension of the liquid. Reduced surface tension in the liquid phase lowers its wicking tension along the fibers (surface tension X cosine of the contact angle). Lower wicking tension reduces the wicking velocity and, in turn, the wicking flux through or along the porous fabric (amount of fluid per unit time per unit cross sectional area). Reduced wicking flux can result in lower fluid handling performance to the end user.

Reduced surface tension in the liquid phase also increases its ability to wet fiber surfaces which are intentionally hydrophobic. Once a formerly hydrophobic fiber is wetted, it can begin exhibiting hydrophilic behavior. A hydrophobic surface which otherwise would have repelled a fluid such as water can pass the fluid through or along the fiber via wicking tension force, gravitational force, pressure gradient force, or other forces.

An alternative to reducing fluid surface tension for the purposes of improving the extent to which nanoparticulate dispersions wet a soft surface is to increase surface energy of the soft surface. Therefore, in certain embodiments, the surface energy of the surface can be increased by applying certain high energy surface treatment to the material to form a treated surface. High energy surface treatment can include, but is not limited to: corona discharge treatment, plasma treatment, UV radiation treatment, ion beam treatment, electron beam treatment, certain laser treatments including pulsed lasers, and other irradiative techniques, provided the surface energy of a portion of some of the fibers is increased. Care is taken to avoid adversely affecting the material to be treated. In some cases, it may be desirable for some of these treatments to be applied to both sides of a soft surface. In addition, it is contemplated that this optional step may be a separate, pretreatment step from the application of the coating composition to the soft surface, or these two steps may be combined.

High energy surface treatments which increase surface energy are useful in that in combination with the nanoparticles they can provide the surface with durable hydrophilic properties. In turn, increased surface energy increases the wettability of the soft surface without use of surfactants in the dispersion to achieve wetting. Avoiding use of surfactant is useful for reasons previously discussed. In a non-limiting example, corona treatment places transient charges on fibrous thermoplastic surfaces. As discussed earlier, partial or full charges dissipate over time, and maintaining partial or full charges on fibrous thermoplastic surfaces is a common limitation. However, it has been found that corona treatment in combination with the nanoparticles can be used to place a durable charge on the material so that water continues to be attracted to the material after time elapses. The use of nanoparticles in conduction with high energy surface treatments, can convert the transient properties of such treatments to more durable properties. In a non-limiting example, corona treatment of a 13 gram per square meter hydrophobic SMS polypropylene nonwoven subsequently treated with a nanoparticulate dispersion and dried exhibited consistently fast strikethrough following multiple insults. Without wishing to be bound by theory, the corona treatment increased the surface energy to the fiber. The nanoparticle dispersion without a surfactant was brought into contact with the fiber surfaces before the charges could dissipate. The higher surface energy enabled the dispersion to wet the fibrous surfaces better than would have been possible without the corona treatment. On the surfaces which are wetted, the nanoparticles associate with the partial or full charge on the surface which would otherwise be transient. This association may take the form of a van der Waals interaction or the form of some other interaction or bond. The nanoparticles are sufficiently small to render the associations sufficiently strong to withstand multiple strikethroughs. The nanoparticle is sufficiently large to resist rotation away from oxygen into the polymer or dissipate in general as previously discussed. The nanoparticles need the high energy surface treatment to enable wetting without a surfactant and provide uniform deposition on drying; the high energy surface treatment needs the nanoparticles to render a durably charged surface.

The materials that have been subjected to a high energy surface treatment and have composite material deposited thereon can be suitable for a great many uses including, but not limited to use to transport liquid in articles such as absorbent articles containing hydrophobic or borderline hydrophilic fibers and in portions of disposable absorbent articles. The portions of disposable absorbent articles include, but are not limited to, topsheets, acquisition layers, distribution layers, wicking layers, storage layers, absorbent cores, absorbent core wraps and containment structures.

In alternative embodiments, other methods can be used to enhance the ability of the surface of the material to receive the coating composition. These include, but are not limited to: providing a pressure gradient on the material (including, but not limited to through the use of pressure rolls, printing rolls, nip rolls, hydrostatic pressure, etc.); reducing the surface tension of the coating composition on the surface without using a surfactant (e.g., such as by using ethanol instead of a surfactant); through the use of "degradable" or "cleavable"

surfactants; and, as described in greater detail below, by inkjet printing of the composition on the material.

The surface may also be referred to herein as the "substrate". Without wishing to be bound by any particular theory or characterization, in some embodiments, the treatments, etc., referred to herein that enhance the ability of the surface to receive the coating composition can be thought of as serving as a "primer" for the surface. The soft surface coating composition may, in some embodiments, be thought of as an aqueous dispersion containing an active material (the composite material). When the coating dries, it leaves an active distribution of composite material on the surface. Again, without wishing to be bound by any particular theory or characterization, in some embodiments, both the primer and the composite material may be interdependent. The composite material distributed on the surface can, in some embodiments, serve to "lock in" the properties of the primer so that such properties are less transient in character, and the primer more effectively allows the nanoparticles to bond to the surface.

There are a non-limiting number of embodiments of methods which use direct or indirect application of the coating composition to the soft surface(s). The term "direct application", as used herein, refers to a method of applying the coating composition directly to the soft surface. Direct application may, for example, include, but is not limited to spraying the coating composition directly on the soft surface(s). The term "indirect application", as used herein, refers to applying the coating composition to some other article, which applies the coating composition to the soft surface(s). Indirect application may, for example, include, but is not limited to, applying the coating composition onto a roll, which applies the coating composition onto the soft surface(s).

In one non-limiting embodiment, an effective amount of a liquid soft surface coating composition is alternatively sprayed onto soft surfaces and/or soft surface articles that include, but are not limited to: absorbent articles, including those having synthetic and naturally fibers, etc. When the coating composition is sprayed onto a soft surface, an effective amount of the composite material may be deposited onto the soft surface, with the soft surface becoming damp or totally saturated with the coating composition. Applying the coating composition to a surface, such as a soft surface, by spraying, can provide a number of benefits. The coating composition can, if desired: be targeted to a particular area of the article to which it is applied; only be applied to one side of an article (as opposed to immersion processes); and can be more efficient in that more of the composite material will end up on the surface rather than being washed down a drain in a washing or rinsing process.

The coating composition can also be applied to a surface such, as a soft surface, via a dipping and/or soaking process in an immersion container followed by an optional drying step. The application can be performed by large-scale processes on soft surfaces and/or finished articles in an industrial application, or in a consumer's home.

In another non-limiting embodiment, the coating composition can be applied to the soft surface(s) by printing the coating composition onto the soft surface(s). Any suitable printing technology can be used for this purpose including, but not limited to: transfer printing such as rotary, gravure, and flexographic printing, and ink jet printing. Inkjet printing is of particular interest because the relatively high inertial force of the small droplets is capable of distributing the coating composition along the substrate surface(s) temporarily enhancing the ability of the coating composition to wet the soft surface(s). The low thermal mass of the droplets enables rapid evaporation of the carrier medium, typically beginning in about 0-10 seconds, preferably in about 0.1 to 1 second or less. The carrier medium begins evaporating before the surface tension of the droplet can fully recover from being spread following impact. The composite material remains where the dispersion had wet the surface prior to evaporation of the carrier medium. Ink jet printing of dispersions as described is beneficial on hydrophobic surfaces, borderline hydrophilic surfaces, and on surfaces in which the advancing contact angle is substantially greater than the receeding contact angle.

The coating composition can be produced in a relatively low viscosity dispersion (e.g., less than about 10 centipoise when needed, preferably less than about 5 centipoise) so that it will flow through the ink jet nozzles and across the surface with less flow resistance than if the viscosity were higher. Unlike conventionally sized particles in conventional dispersions, nanoparticles are sufficiently small that they will not settle in the low viscosity medium and they will not clog the nozzles of the inkjet printer. Any suitable type of inkjet printing technology can be used including, but not limited to, drop on demand ink jet printers such as drop vaporization type with oscillating heating elements and drop ejection type with mechanical pump and oscillating crystal. In some embodiments, soft surfaces, and other articles can be moved through or past the ink jet printing nozzles. In other embodiments, such as in the case of hard surfaces, the ink jet printer can be configured to move relative to the surface.

In some embodiments, it may be desirable for the composite material to have a refractive index of greater than or equal to about 1.3. In some embodiments, it may be desirable for the composite material to have a refractive index of less than or equal to about 5.5. The refractive index of the composite material can be measured using the bulk composite material or a thin film of the bulk material using ellipsometery.

It has been found that, in some embodiments, the darkening of the soft surface generally increases with increasing particle sizes. Of course, the particles used should not be so large that they are visible on the soft surface.

The coating composition may, in some embodiments, be applied so that after the coating composition dries, the composite material covers greater than or equal to about 0.5% of the surface area of the soft surface.

The present invention also relates to an article of manufacture comprising the soft surface coating composition of the present invention in a package. The coating composition may be provided in association with instructions for how to use the coating composition to treat soft surfaces such that the soft surfaces are modified, in order to obtain at least one of the desirable results described herein.

In one non-limiting embodiment, the article of manufacture comprises the soft surface coating composition in a spray dispenser, in association with instructions for how to use the coating composition to treat soft surfaces correctly, including, e.g., the manner and/or amount of composition to spray, and the preferred ways of applying the coating composition, as will be described with more detail herein below. It is important that the instructions be as simple and clear as possible, which includes using pictures and/or icons where desirable.

The soft surface coating composition may be placed into a spray dispenser in order to be distributed onto a soft surface. The spray dispenser can be any of the manually activated types for applying the coating composition to surface areas and/or a number of substrates, as well as non-manually operated, powered sprayers for conveniently applying the coating composition to large hard surface areas and/or a large number of substrates. The spray dispenser can include, but are not limited to, any of the following: aerosol spray dispensers, self-pressurized spray dispensers, non-aerosol, manually activated, pump-spray dispensers, manually-activated trigger-spray dispensers, trigger sprayers or finger pump sprayers, non-manually operated spray dispensers including, but not limited to, powered sprayers, air aspirated sprayers, liquid aspirated sprayers, electrostatic sprayers, and nebulizer sprayers. Powered sprayers can include, but are not limited to, centrifugal or positive displacement designs. Other types of sprayers, including, but not limited to, electrostatic sprayers, may reduce foaming and form suitable coatings with less visible residue under a wider variety of conditions. This may allow a wider range of surfactants to be used in the coating composition.

The present invention also relates to an article of manufacture comprising a soft surface coating composition for use in spraying and/or misting an entire soft surface or article in such a manner that excessive amounts of the coating composition are prevented from being released to the open environment, provided in association with instructions for use to ensure that the consumer applies at least an effective amount of coating composition, to provide the desired soft surface multi-use benefit.

The present invention also encompasses the inclusion of instructions on the use of the soft surface coating compositions of the present invention with the packages containing the coating compositions herein or with other forms of advertising associated with the sale or use of the coating compositions. The instructions may be included in any manner typically used by consumer product manufacturing or supply companies. Examples include providing instructions on a label attached to the container holding the coating composition; on a sheet either attached to the container or accompanying it when purchased; or in advertisements, demonstrations, and/or other written or oral instructions which may be connected to the purchase or use of the coating compositions.

Specifically the instructions include a description of the use of the coating composition, for instance, the recommended amount of composition to use in order to coat the surface or article; the recommended amount of composition to apply to the surface; if spraying, soaking or rubbing is appropriate.

The coating compositions can be included in a product.

All parts, percentages and ratios used herein are expressed as percent weight unless otherwise specified.

Even though the compositions and methods of the present invention are focused on domestic modification of soft surfaces, the compositions and methods of the present invention can be used for industrial modification of soft surfaces, such as in textile mills.

The disclosure of all patents, patent applications (and any patents which issue thereon, as well as any corresponding published foreign patent applications), and publications mentioned throughout this description are hereby incorporated by reference herein. It is expressly not admitted, however, that any of the documents incorporated by reference herein teach or disclose the present invention.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

The entire contents of all patents and patent applications listed above are incorporated here in reference.

EXAMPLES

Example 1

In order to deposit silver metal on nanoclay, silver ions were reduced in the presence of Laponite using the Tollen's reagent, which is able to undergo reduction by either an aldehyde or ketone to form silver metal via the following reaction:

$$Ag(NH_3)_2OH + glucose \rightarrow Ag^0$$

The Tollen's reagent was prepared by adding two drops of 10% NaOH to 5 mL of 5% $AgNO_3$ to form a gray-brown precipitate. This precipitate was then dissolved by the dropwise addition of 2% $NH_4OH$ to yield a total Tollen's reagent volume of 30 mL.

A solution of silver-coated Laponite was prepared by adding 600 mg of Laponite to 50 mL of distilled water and using a magnetic stirrer to exfoliate for 20 minutes. To this solution, 800 mg of glucose were added and the stirring continued for 10 minutes to ensure complete dissolution of the glucose. To this, 10 mL of Tollen's reagent as prepared above were added. After two hours of continuous stirring, the solution turned golden yellow in color. Further reaction time yielded a dark amber-brown solution. Samples prepared for particle size analysis and TEM analysis were diluted by a factor of 10 to prevent particle aggregation. The particle size of the nanoparticles dictates the color of the solution caused by a surface plasmon resonance phenomenon. For silver particles, a yellow color has been determined to have the smallest particle size possible.

Example 2

An absorbent article having the configuration shown in FIG. 1 is made as follows. The cover is made of a 75 gsm spunlace body facing layer made from 75% polyester and 25% rayon (3P075V25P75 from Spuntech Industries Ltd., Upper Tiberias, Israel). The backsheet is a 30 gsm microporous polyethylene backsheet (01030A1-1-1-1-2, FullSafe, Manila, Philippines). It is treated with a soft surface coating composition according to the invention. The soft surface coating composition comprises the silver-loaded nanoclay as made in Example 1. In addition, the coating composition comprises a surfactant and an aqueous carrier material. The coating composition is applied to the absorbent core by spraying.

We claim:

1. A soft surface coating composition comprising: 1) a composite material comprising (a) an exfoliated nanoparticle having a surface and (b) a metal selected from Groups 3 to 12, aluminum and magnesium, wherein the metal is loaded onto the surface of the nanoparticle; 2) a carrier medium; 3) a surfactant; and 4) one or more adjunct ingredients, and wherein the metal is in the neutral (0) metal state.

2. An absorbent article comprising a composite material comprising (a) an exfoliated nanoparticle having a surface and (b) a metal selected from Groups 3 to 12, aluminum and magnesium, wherein the metal is loaded onto the surface of the nanoparticle and is in the neutral (0) metal state.

* * * * *